United States Patent [19]

Wang

[11] Patent Number: 4,940,801

[45] Date of Patent: Jul. 10, 1990

[54] SPIRODILACTAM DERIVATIVES

[75] Inventor: Pen C. Wang, Houston, Tex.

[73] Assignee: Shell Oil Company, Houston, Tex.

[21] Appl. No.: 356,158

[22] Filed: May 24, 1989

Related U.S. Application Data

[63] Continuation-in-part of Ser. No. 314,512, Feb. 23, 1989, Pat. No. 4,885,351.

[51] Int. Cl.$^5$ .......................................... C07D 487/10
[52] U.S. Cl. .................................................... 548/410
[58] Field of Search ......................................... 548/410

[56] References Cited

U.S. PATENT DOCUMENTS 4,100,140  7/1978  Zahir et al. ............................ 526/90
4,740,561  4/1988  Tsujimoto et al. ................ 525/327.6
4,745,197  5/1988  Eisenbarth et al. .................. 548/521

Primary Examiner—Robert T. Bond

[57] ABSTRACT

Novel unsaturated derivatives of 1,6-diaza [4,4] spirodilactams having a monovalent unsaturated substituent on each spiro ring nitrogen atom are produced by reaction of an unsaturated amine and a spirodilactam precursor selected from a 4-oxoheptanedioic acid compound or a 1,6-dioxo [4,4] spirodilactone.

49 Claims, No Drawings

SPIRODILACTAM DERIVATIVES

RELATED APPLICATION

This application is a continuation-in-part of copending U.S. patent application Ser. No. 314,512, filed Feb. 23, 1989, now U.S. Pat. No. 4,885,351.

FIELD OF THE INVENTION

This invention relates to a novel class of unsaturated derivatives of a 1,6-diaza [4.4] spirodilactam and to the process for the production thereof. More particularly, the invention relates to 1,6-diaza [4.4] spirodilactam derivatives having an alkenyl or an alkynyl substituent on each of the spiro ring nitrogen atoms.

BACKGROUND OF THE INVENTION

Unsaturated derivatives of a wide variety of organic compounds are known to be curable upon heating with a curing agent to thereby produce crosslinked products which exhibit good solvent resistance and mechanical properties as well as relatively high heat distortion temperatures. Such unsaturated derivatives are cured with catalytic or stoichiometric polyfunctional curing agents or by exposure to high intensity energy to produce tough, heat resistant thermoset resins which are processed by conventional methods into sheets, laminates with fiber glass or other reinforcement or shaped articles and the thermoset resins are also useful in adhesive formulations.

Among unsaturated derivatives known to cure or crosslink by conventional technology are allyl or propargyl ethers of bisphenols. The disclosure of Zahir et al, U.S. Pat. No. 4,100,140 is illustrative. The compound 2,2-di(4-hydroxyphenyl)propane, also known as bisphenol A or BPA, is converted to the sodium salt and reacted with allyl chloride to produce the diallyl ether of BPA, i.e., 2,2-di(4-allyloxyphenyl)propane. This diallyl compound is curable by reaction with, for example, a bis(maleimide) curing agent.

On some occasions, the cured products which produce the more desirable properties, particularly in high temperature applications, are produced from unsaturated derivatives of polycyclic structure. It would be of advantage to provide a novel class of unsaturated derivatives having a plurality of rings within the molecular structure.

SUMMARY OF THE INVENTION

The present invention provides a novel class of 1,6-diaza [4.4] spirodilactam derivatives, wherein each spiro ring nitrogen atom has a substituent with terminal alkenyl or alkynyl unsaturation. More particularly, the invention relates to a process of producing the unsaturated spirodilactam derivatives by reacting a terminally-unsaturated primary amine with a spirodilactam precursor selected from ketodiacid compounds or spirodilactones.

DESCRIPTION OF THE INVENTION

The novel monomeric unsaturated spirodilactam derivatives of the invention are produced by reaction of a terminally-unsaturated primary amine compound and a spirodilactam precursor selected from 4-oxoheptandioic acid compounds or 1,6-dioxa [4.4] spirodilactones.

In the modification where the precursor of the spirodilactam is a ketodicarboxylic acid compound, a variety of such compounds having a variety of substituents in addition to the keto group and the carboxy functions are suitably employed as the spirodilactam precursor. The preferred ketodiacid compounds are 4-oxoheptanedioic acid compounds of up to 30 carbon atoms represented by the formula

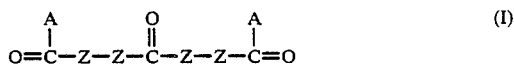

where A independently is hydroxy, lower alkoxy of up to 4 carbon atoms inclusive or halo preferably the middle halogens chloro or bromo, and Z independently is $>C(Z')_2$ in which $Z'$ independently is hydrogen, lower alkyl of up to 4 carbon atoms, preferably methyl, halo, preferably the lower halogens fluoro or chloro, or aryl, preferably phenyl, or Z is such that two adjacent Z groups taken together form a ring system $Z''$ of from 5 to 7 ring atoms up to two of which are heteroatoms selected from nitrogen, oxygen or sulfur with the remainder of the ring atoms being carbon atoms, there being up to 15 carbon atoms in each $Z''$, two of which form a bridge between the carbon atoms connected by the adjacent Z groups. When adjacent Z groups taken together are $Z''$, the ring system is aromatic, cycloaliphatic or heterocyclic, the ring system is saturated or unsaturated and is otherwise hydrocarbyl containing only atoms of carbon and hydrogen besides any heteroatom ring atoms or is substituted hydrocarbyl additionally containing other atoms in the form of inert carbon atom substituents, for example, halogen atoms and preferably the middle halogens.

In one embodiment employing the oxoheptanedioic acid compounds as the precursor of the spirodilactam of the invention, each Z is acyclic or not a part of a ring, i.e., Z is $>C(Z')_2$, and the spirodilactam is a 4-oxoheptanedioic acid compound represented by the formula

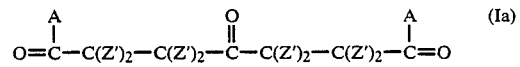

wherein A and $Z'$ have the previously stated meanings. Such 4-oxoheptanedioic acid compounds include 4-oxoheptanedioic acid, dimethyl 4-oxoheptanedioate, 2,6-dimethyl-4-oxoheptanedioic acid, 2,3,5,6-tetramethyl-4-oxoheptanedioyl chloride, diethyl 2-phenyl-4-oxoheptanedioate, di-n-propyl 2,6-di-n-butyl-4-oxoheptanedioate and 6-carbomethoxy-3,3,5,5-tetramethyl-4-oxohexanoic acid. The preferred acid compounds of formula Ia are those wherein each $Z'$ is hydrogen or methyl, more preferably hydrogen, and wherein each A substituent is hydroxy or alkoxy, more preferably hydroxy.

These 4-oxoheptanedioic acid compounds are known compounds or are produced by known methods. Certain of the esters of formula Ia, i.e., the compounds wherein A is alkoxy, are conveniently produced by reaction of formaldehyde and an unsaturated carboxylic acid ester such as methyl acrylate, ethyl methacrylate, methyl crotonate, methyl ethacrylate and propyl 2,3-dimethyl-2-butenoate. This reaction is conducted in the presence of a thiazolium salt and a tertiary amine and produces the dialkyl 4-oxoheptandioate derivative in good yield. This process is described more fully and is claimed U.S. Pat. No. 4,800,231 incorporated herein by reference. Conversion of the esters thereby obtained to the corresponding acids or acid halides is by conventional methods.

In a second embodiment of the 4-oxoheptanedioic acid compounds as the spirodilactam precursor, the 4-oxoheptanedioic acid compound incorporates a fused ring substituent between the keto group and each carboxy function, i.e., adjacent Z groups are Z". Such diacid compounds are represented by the formula

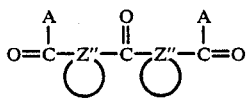
(Ib)

wherein A and Z" have the previously stated meanings. Illustrative of these cyclic ketodiacid compounds are di(2-carboxyphenyl) ketone, di(2-carboxycyclohexyl) ketone, di(2-carbopropoxycyclo-3-pentenyl) ketone, di(2-chlorocarbonylphenyl) ketone, di(2-carboxy-3-pyridyl) ketone, 2-carboxyphenyl N-methyl-3-carboxy-2-pyrrl ketone, di(3-carbethoxy-2-morpholyl) ketone and di(2-carbomethoxy-3-chlorophenyl) ketone. The preferred cyclic ketodiacids of formula Ib are those wherein each Z" is a fused ring system of from 5 to 6 ring atoms including up to 1 nitrogen atom, and particularly those compounds wherein Z" is benzo. The cyclic ketodiacids of formula Ib are known compounds or are produced by known processes, for example, the process of Conover et al, U.S. Pat. No. 1,999,181, or the method of Cava et al, J. Am. Chem. Soc., 20, 6022 (1955).

In yet another embodiment of the ketodiacid compounds as the spirodilactam precursor, the 4-oxoheptanedioic acid compounds incorporate one cyclic Z" moiety with the remainder of the Z groups being >C(Z')$_2$,
i.e., the compounds of the formula

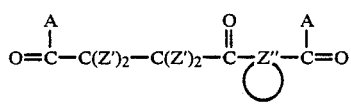
(Ic)

wherein A, Z' and Z" have the previously stated meanings. Such ketodiacids of one fused cyclic substituent are illustrated by 3-(2-carboxybenzoyl)propionic acid, 3-(2-carbomethoxybenzoyl)propionic acid, 3-(2-carbomethoxypyridyloxy)-2-ethylpropionic acid, ethyl 3-(2-carbethoxybenzoyl)propionate and 3-(2-carboxy-4-methylbenzoyl)butyrl chloride. The ketodiacids of formula Ic are known compounds or are produced by known methods. For example, 2-carbomethoxybenzaldehyde reacts with methyl acrylate by the general teachings of U.S. Pat. No. 4,800,231 to produce methyl 3-(2-carbomethoxybenzoyl)propionate.

In a second modification, the spirodilactam precursor is a 1,6-dioxaspiro[4.4]nonane-2,7-dione compound in which each spiro ring is substituted with hydrogens or other monovalent groups or which incorporate a cyclic fused ring substituent on one or both of the spiro rings. One class of such 1,6-dioxa [4.4]spirodilactones is represented by the formula

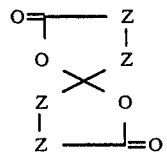
(II)

wherein Z has the previously stated meaning.

In the embodiment of the spirodilactone as the spirodilactone as the spirodilactam precursor wherein each Z is acyclic as not being a part of a fused ring, i.e., Z is >C(Z')$_2$, the spirodilactone is represented by the formula

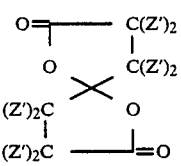
(II)

wherein Z has the previously stated meaning. Illustrative of such spirodilactams are 1,6-dioxaspiro[4.4]nonane-2,7-dione, 3,8-dimethyl-1,6-dioxaspiro[4.4]nonane-2,7-dione, 3,9-diphenyl-1,6-dioxaspiro[4.4]nonane-2,7-dione 3,9-diphenyl-1,6-dioxaspiro[4.4]nonane-2,7-dione, 3,4,8,9-tetramethyl-1,6-diazaspiro[4.4]nonane-2,7-dione, 4,9-diethyl-1,6-dioxaspiro[4.4]nonane-2,7-dione, 3,3,4,4,8,8,9,9-octamethyl-1,6-dioxaspiro[4.4]nonane-2,7-dione and 3,4,8,9-tetrafluoro-1,6-dioxaspiro[4.4]nonane-2,7-dione. The preferred spirodilactones of the above formula IIa are those wherein at least one and preferably both of the Z' substituents on each Z'-substituted carbon atom are hydrogen. The compounds of formula IIa are known compounds or are produced by known methods, for example, the process of Pariza et al, Synthetic Communications, Vol. 13 (3), pp. 243–254 (1983), incorporated herein by reference.

In the embodiment of the spirodilactones as spirodilactam precursors of the above formula II which incorporate a fused ring substituent on each of the two spiro rings, the spirodilactones are represented by the formula

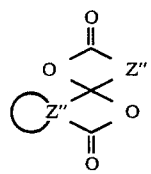
(IIb)

wherein Z" has the previously stated meaning. Typical compounds of formula IIb are 3,4,8,9-dibenzo-1,6-dioxaspiro[4.4]nonane-2,7-dione, 3,4,8, 9-di(cyclopentano)-1,6-dioxaspiro[4.4]nonane-2,7-dione, 3,4,8,9-di(4-methyl-benzo)-1,6-dioxaspiro[4.4]nonane-2,7-dione and 3,4,8,9-di(pyrido)-1,6-dioxaspiro[4.4]nonane-2,7-dione. The preferred spirodilactones of formula IIb are those wherein each Z" has from 5 to 6 ring atoms including up to one nitrogen atom. Particularly preferred as the Z" moiety is benzo. The compounds are known compounds or are produced by known methods such as that of the above Cava et al article or by the process of U.S. Pat. No. 1,999,181.

In a third embodiment of the use of a spirodilactone as a spirodilactam precursor, a fused cyclic substituent is located on one spiro ring and the other spiro ring is free of fused cyclic substituents. Such spirodilactones are represented by the formula

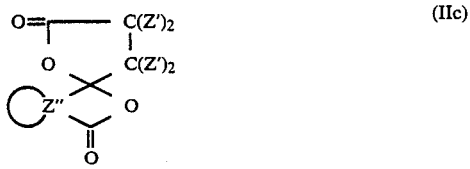
(IIc)

wherein Z' and Z" have the previously stated meanings. Such spirodilactones are illustrated by 3,4-benzo-8-methyl-1,6-dioxaspiro[4.4]nonane-2,7-dione and 3,3,4,4-tetramethyl-8,9-morpholo-1,6-dioxaspiro[4.4]nonane-2,7-dione. The preferred spirodilactone of formula IIc is 3,4-benzo-1,6-dioxaspiro[4.4]nonane-2,7-dione. These spirodilactones are known materials or are produced by known methods, for example, by the dehydration of the corresponding ketodiacid. By way of specific illustration, 3,4-benzo-1,6-dioxaspiro[4.4]nonane-2,7-dione is produced by dehydration of 3-(2-carboxybenzoyl)propionic acid through application of heat.

In general, the preferred spirodilactones are those which are free from fused ring substituents (formula Ia) or which incorporate a fused ring substituent on each spiro ring (formula IIb). An especially preferred member of the former class is 1,6-dioxaspiro[4.4]nonane-2,7-dione and 3,4,8,9-dibenzo-1,6-dioxaspiro[4.4]nonane-2,7-dione is an especially preferred member of the latter class.

The spirodilactam precursor, regardless of the particular structure, is reacted according to the process of the invention with a primary amine having terminal unsaturation separated from the primary amino group by one carbon atom or by an aromatic ring. While a variety of unsaturated amines having a variety of structures are suitable in the process, a preferred class of unsaturated primary amines are the hydrocarbyl amines represented by the formula

where E is $CH_2=CX'$— or $HC\equiv C$— and X is phenylene or $-C(X')_2-$ in which X' is hydrogen or lower alkyl of up to 4 carbon atoms. Illustrative of such primary amino compounds are allylamine, propargylamine, p-vinylaniline, methallylamine, m-aminophenylacetylene, 3-amino-1-butene, 3-amino-1-hexyne, 3-amino-3-methyl-1-heptene and 3-amino-2-ethyl-1-propene. The preferred unsaturated primary amines are those wherein X is $-C(X')_2-$ in which X' is hydrogen. These are allylamine and propargylamine, of which allylamine is particularly preferred.

The production of the spirodilactams having an unsaturated substituent on each spiro ring nitrogen is accomplished by contacting the unsaturated primary amine and the spirodilactam precursor under reaction conditions in a liquid phase in the presence of a reaction diluent. The reactants combine to form the substituted spirodilactam in a molar ratio of 2:1 although in practice the unsaturated primary amine and the spirodilactam precursor reactants are provided to the reaction mixture in molar ratios of from about 8:1 to about 1:2. Reactant ratios that are substantially stoichiometric, i.e., from about 2.5:1 to about 2:1.5 are preferred. The reaction diluent is an inert reaction diluent which is liquid under reaction conditions and which is capable of dissolving at least a portion of each reactant at reaction temperature. Suitable reaction diluents include ethers, e.g., acyclic ethers such as diethylene glycol dimethyl ether and tetraethylene glycol dimethyl ether as well as cyclic ethers such as tetrahydrofuran and dioxane, chlorinated hydrocarbon diluents such as methylene chloride, chloroform and chlorobenzene, sulfur-containing diluents such as dimethyl sulfoxide and sulfolane and N-alkylamides such as N,N-dimethylformamide, N,N-dimethylacetamide and N-methyl-2-pyrrolidone. It is often useful to choose a diluent, or employ a second diluent such as an alkylated benzene, e.g., toluene or ethylbenzene, with which water forms an azetrope. It is thereby possible to remove the water present or formed in the reaction mixture as an often low-boiling azeotrope. Removal of water by conventional fractionation or by extraction is also suitable. The reaction temperature to be employed is typically from about 50° C. to about 250° C. but more often from about 125° C. to about 200° C. A suitable reaction pressure is one which will maintain the reaction mixture in the liquid phase at reaction temperature. Such pressures are up to about 20 atmospheres but preferably are from about 0.8 atmosphere to about 10 atmospheres. Subsequent to reaction the unsaturated spirodilactam product is recovered by conventional methods such as extraction, solvent removal or precipitation.

The unsaturated derivatives of the 1,6-diaza[4.4] spirodilactam are adducts of the unsaturated primary amine and the spirodilactam precursor, i.e., 1,6-diaza[4.4] spirodilactams, having an unsaturated substituent on each spiro ring nitrogen atom wherein the unsaturation is terminal and is separated from the nitrogen to which the substituent is attached by one carbon atom or by an aromatic ring. In term of the preferred spirodilactam precursors (formula I or II) and the primary amine reactants (formula III) the spirodilactam products are represented by the formula

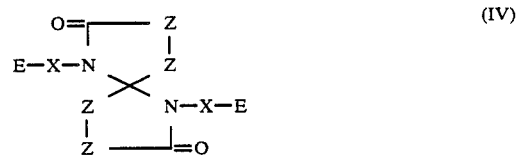
(IV)

wherein Z, E and X have the previously stated meanings. Illustrative of such unsaturated spirodilactams are 1,6-diallyl-1,6-diazaspiro[4.4]nonane-2,7-dione, 1,6-dipropargyl-3,8-dimethyl-1,6-diazaspiro[4.4]nonane-2,7-dione, 1,6-di(4-styryl)-1,6-diazaspiro[4.4]nonane-2,7-dione, 1,6-di(1-methyl-2-propenyl-3,4,8,9-dibenzo-1,6-diazaspiro[4.4]nonane-2,7-dione, 1,6-di[3-(2-propynyl)-phenyl]-1,6-diazaspiro[4.4]nonane-2,7-dione and 1,6-di(2-butyl-2-propenyl)-3,3-dimethyl-1,6-diazaspiro[4.4]nonane-2,7-dione. The identity of other spirodilactam products will be apparent from consideration of the above formulas for the reactants and the spirodilactam product. Particularly preferred are the 1,6-diallyl spirodilactam products.

The unsaturated spirodilactam derivatives find utility as thermosetting resins or toughening agents and are employed in the production of cured or crosslinked products useful in surface coatings, adhesive formulations and in fiber-reinforced composites where the reinforcement is glass or carbon. The cured products are additionally useful as casting or impregnating resins. Such products are produced by processing the cured products by methods known to be useful for thermoset resins. The curing of the unsaturated spirodilactam products is accomplished by conventional methods such as thermal or photochemical excitation, by catalyzed polymerization employing cationic or anionic catalysts or by reaction with a polyfunctional curing agent. The curing process is conducted by heating a mixture of the spirodilactam derivative and the curing agent to a temperature above about 150° C. but below about 300° C. It is frequently useful to conduct the heating in stages as by heating the composition to be cured to a relatively low curing temperature to initiate the curing process and subsequently raise the temperature to a higher curing temperature to complete the cure. This process of curing in stages is conventional for the curing of thermoset resins.

The invention is further illustrated by the following Illustrative Embodiments which it should not be construed as limiting the invention.

ILLUSTRATIVE EMBODIMENT I

A mixture of 150 g (0.86 mole) of 4-oxoheptandioic acid, 100 g (1.75 mole) of allylamine, 200 ml of N,N-dimethylacetamide and 50 ml of toluene is placed in a 500 ml round bottom flask equipped with a mechanical stirrer and a condenser. The mixture is warmed, while stirred, to 140°–160° C. and maintained at this temperature for 16 hours while the water present or formed is removed by azeotropic distillation. The resulting mixture was cooled and the N,N-dimethylacetamide was removed under reduced pressure. The crude product was then dissolved in chloroform and washed several times with water. Removal of the chloroform provided 200.8 g thick amber liquid product. The nuclear magnetic resonance spectra of the products were consistent with the structure N,N'-diallyl-1,6-diazaspiro[4.4]nonane-2,7-dione.

ILLUSTRATIVE EMBODIMENT II

A mixture of 50 parts by weight of the product of illustrative Embodiment I and 50 parts by weight of di(4-maleimidophenyl)methane was melted at a temperature of 100°–120° C. The mixture was then heated in an oven at 200° C. for 4 hours and at 220° C. for an additional 2 hours. The resulting crosslinked product had a glass transition temperature of 237° C.

What is claimed is:

1. A substituted 1,6-diaza 4.4]spirodilactam having an unsaturated substituent on each spiro ring nitrogen atom, which unsaturation is terminal, hydrocarbyl and is separated from the nitrogen atom to which the substituent is attached by one carbon atom or by an aromatic ring.

2. The spirodilactam of claim 1 represented by the formula

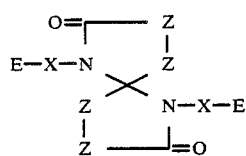

(IV)

wherein Z independently is $>C(Z')_2$ in which Z' independently is hydrogen, lower alkyl, lower halo or phenyl, or Z is such that two adjacent Z groups taken together form a ring system Z" of from 5 to 7 ring atoms up to two of which are heteroatoms selected from nitrogen oxygen or sulfur with the remainder of the ring atoms being carbon atoms, there being up to 15 carbon atoms in each Z", two of which form a bridge between the carbon atoms connected by the adjacent Z groups, E independently is $CH_2=CX'-$ or $CH\equiv C-$ and X is phenylene or $-C(X')_2-$ in which X' is hydrogen or lower alkyl.

3. The spirodilactam of claim 2 wherein E is $CH_2=CX'-$.

4. The spirodilactam of claim 3 wherein X is $-C(X')_2-$.

5. The spirodilactam of claim 4 wherein Z is $>C(Z')_2$.

6. The spirodilactam of claim 5 wherein X' is hydrogen.

7. The spirodilactam of claim 6 wherein Z' is hydrogen or methyl.

8. The spirodilactam of claim 6 wherein Z' is hydrogen.

9. The spirodilactam of claim 4 wherein adjacent Z groups are Z".

10. The spirodilactam of claim 9 wherein X' is hydrogen.

11. The spirodilactam of claim 10 wherein Z" is benzo.

12. The spirodilactam of claim 2 wherein E is $CH\equiv C-$.

13. The spirodilactam of claim 12 wherein X is $-C(X')_2$ in which X' is hydrogen.

14. The spirodilactam of claim 13 wherein Z is $>C(Z')_2$.

15. The spirodilactam of claim 14 wherein Z' is hydrogen.

16. The spirodilactam of claim 13 wherein adjacent Z groups are Z".

17. The spirodilactam of claim 16 wherein Z" is benzo.

18. The process of producing an unsaturated derivative of a 1,6-diaza [4.4] spirodilactam by contacting, under reaction conditions, an unsaturated primary amine of the formula $$E-X-NH_2$$

wherein E is $CH_2=CX'-$ or $CH\equiv C-$, X is phenylene or $-C(X')_2$ in which X' independently is hydrogen or lower alkyl, with the spirodilactam precursor selected from the 4-oxoheptandioic acid compound of the formula

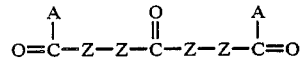

or the 1,6-dioxa [4.4] spirodilactone of the formula

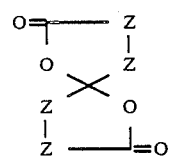

wherein A independently is hydroxy, lower alkoxy or middle halo and Z independently is >C(Z')$_2$ in which Z' independently is hydrogen, lower alkyl, lower halo or phenyl, or Z is such that two adjacent Z groups taken together form a ring system Z" of from 5 to 7 ring atoms up to two of which are heteroatoms selected from nitrogen, oxygen or sulfur with the remainder of the ring atoms being carbon atoms, there being up to 15 carbon atoms in each Z", two of which form a bridge between the carbon atoms connected by the adjacent Z groups.

19. The process of claim 18 wherein the spirodilactam precursor is a 4-oxoheptandioic acid compound.

20. The process of claim 19 wherein E is CH$_2$=CX'—.

21. The process of claim 20 wherein Z is >C(Z')$_2$.

22. The process of claim 21 wherein X is —C(X')$_2$—.

23. The process of claim 22 wherein Z' is hydrogen or methyl.

24. The process of claim 23 wherein X' is hydrogen.

25. The process of claim 24 wherein Z' is hydrogen.

26. The process of claim 20 wherein adjacent Z groups are Z".

27. The process of claim 26 wherein Z" is benzo.

28. The process of claim 27 wherein E—X— is allyl.

29. The process of claim 19 wherein E is CH≡C—.

30. The process of claim 19 wherein E—X— is propargyl.

31. The process of claim 30 wherein Z is >C(Z')$_2$.

32. The process of claim 31 wherein Z' is hydrogen.

33. The process of claim 18 wherein the spirodilactam precursor is a spirodilactone.

34. The process of claim 33 wherein E is CH$_2$=CX'—.

35. The process of claim 34 wherein Z is >C(Z')$_2$.

36. The process of claim 35 wherein X is —C(X')$_2$—.

37. The process of claim 36 wherein E—X— is allyl.

38. The process of claim 37 wherein Z' is hydrogen or methyl.

39. The process of claim 37 wherein Z' is hydrogen.

40. The process of claim 34 wherein adjacent Z groups are Z".

41. The process of claim 40 wherein E—X— is allyl.

42. The process of claim 41 wherein Z" is benzo.

43. The process of claim 33 wherein E is CH≡C—.

44. The process of claim 43 wherein E—X— is propargyl.

45. The process of claim 44 wherein Z is >C(Z')$_2$.

46. The process of claim 45 wherein Z' is hydrogen or methyl.

47. The process of claim 46 wherein Z' is hydrogen.

48. The process of claim 47 wherein adjacent Z groups are Z".

49. The process of claim 48 wherein Z" is benzo.

* * * * *